United States Patent [19]

Damour et al.

[11] Patent Number: 5,563,144
[45] Date of Patent: Oct. 8, 1996

[54] ANTISEROTONINS, THEIR PREPARATION AND PHARMACEUTICAL COMPOSITIONS CONTAINING THEM

[75] Inventors: Dominique Damour, Paris; Richard Labaudiniere, Vitry Sur Seine; Jean-luc Malleron, Marcoussis; Serge Mignani, Chatenay-Malabry, all of France

[73] Assignee: Rhone-Poulenc Rorer S.A., Antony, France

[21] Appl. No.: 470,726

[22] Filed: Jun. 6, 1995

Related U.S. Application Data

[63] Continuation of Ser. No. 137,091, filed as PCT/FR92/00354, Oct. 26, 1993 published as WO92/19624, Nov. 12, 1992 abandoned.

[30] Foreign Application Priority Data

Apr. 26, 1991 [FR] France ................... 91 05170

[51] Int. Cl.[6] ................... A61K 31/495; A61K 31/55; A61K 31/445; C07D 239/70; C07D 401/04; C07F 7/02
[52] U.S. Cl. ................... 514/253; 514/63; 514/221; 514/226.5; 514/252; 514/307; 514/321; 514/338; 544/49; 544/229; 544/249; 544/363; 544/368; 546/14; 546/148; 546/198; 546/271.1
[58] Field of Search ................... 544/49, 229, 368, 544/249, 363; 546/14, 148, 198, 270; 514/63, 221, 252, 226.5, 321, 307, 338

[56] References Cited

U.S. PATENT DOCUMENTS 4,104,387  8/1978  Wade et al. ................... 424/250
4,132,725  1/1979  Barcza ................... 424/184

FOREIGN PATENT DOCUMENTS

| 89089 | 9/1983 | European Pat. Off.. |
| 330065 | 8/1989 | European Pat. Off.. |
| 329168 | 8/1989 | European Pat. Off.. |
| 269968 | 10/1990 | European Pat. Off.. |
| 398425 | 11/1990 | European Pat. Off.. |
| 433149 | 6/1991 | European Pat. Off.. |
| 2154520 | 5/1973 | France . |
| 645628 | 10/1984 | Switzerland . |

OTHER PUBLICATIONS

Jean–Luc Malleron et al Journal of Medicinal Chemistry, vol. 34, No. 8, p. 2477 (1991).
Perregaard et al. J. Med. Chem. 1992, 35, 4813–4822.
Leysen et al, Molecular Pharmacology 21: 301–314.

*Primary Examiner*—Cecilia Tsang
*Attorney, Agent, or Firm*—Finnegan, Henderson, Farabow, Garrett & Dunner, L.L.P.

[57] ABSTRACT

This invention relates to compounds having the formula $R_1\text{-}(CH_2)_n\text{-Het}$ wherein $R_1$ is a residue having the formula (B), (C), (D); Het represents a radical phenyl-4 tetrahydro-1,2,3,6 pyridyl-1 whose phenyl cycle is optionally substituted by a halogen atom or an alkyl, alkoxy or hydroxy radical; a radical phenyl-4 piperazinyl-1 whose phenyl cycle is optionally substituted by a halogen atom or an alkyl, alkoxy or hydroxy radical; $R_3$ is a hydrogen atom or a phenyl radical; $R_4$ is a hydrogen or halogen atom or a residue Het; $R_5$ is a carbonyl or sulfonyl radical; $R_6$ is a radical $Si(CH_3)_2$ or $C(CH_3)_2$; n equals 1, 2, 3 or 4; excepting {[(phenyl-4 tetrahydro-1,2,3,6 pyridyl-1)-2 ethyl] amino}-3 benzisothiazol-1,2 dioxyde-1,1; their salts, their preparation and medicaments containing them.

13 Claims, No Drawings

ANTISEROTONINS, THEIR PREPARATION AND PHARMACEUTICAL COMPOSITIONS CONTAINING THEM

This is a continuation of application Ser. No. 08/137,091, filed as PCT/FR92/00354, Oct. 26, 1993 published as WO92/19624, Nov. 12, 1992, now abandoned.

The present invention relates to compounds of formula:

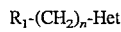  (I)

their preparation and medicinal products containing them.

3-Amino-1,2-benzisothiazole 1,1-dioxide derivatives are described in U.S. Pat. No. 4,104,387 as anti-inflammatory agents.

In the formula (I), $R_1$ represents a residue of formula:

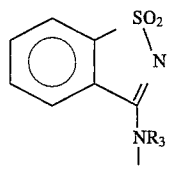  (B)

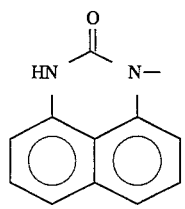  (C)

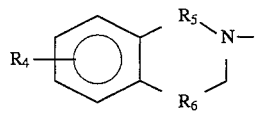  (D)

Het represents
- a radical 4-phenyl-1,2,3,6-tetrahydro-1-pyridyl whose phenyl ring is optionally substituted by a halogen atom or an alkyl, alkoxy or hydroxyl radical,
- a radical 4-phenylpiperidino whose phenyl ring is optionally substituted by a halogen atom or an alkyl, alkoxy or hydroxyl radical,
- a radical 4-phenyl-1-piperazinyl whose phenyl ring is optionally substituted by a halogen atom or an alkyl, alkoxy or hydroxyl radical, $R_3$ represents a hydrogen atom or a phenyl radical $R_4$ represents a hydrogen or a halogen atom or a Het residue, $R_5$ represents a carbonyl or sulphonyl radical, $R_6$ represents a radical Si $(CH_3)_2$ or C $(CH_3)_2$, n is equal to 1, 2, 3 or 4, with the exception of 3-{[2-(4-phenyl-1,2,3,6-tetrahydro-1-pyridyl) ethyl]amino}-1,2-benzisothiazole 1,1-dioxide.

The invention also relates to the salts of the compounds of formula (I) with inorganic or organic acids.

In the definitions above and in those that will be given below, the alkyl and alkoxy radicals contain 1 to 4 carbon atoms in a linear or branched chain, and the halogen atoms are preferably fluorine, chlorine or bromine atoms.

The compounds of formula (I) may be prepared by the action of a derivative of formula:

  (II)

in which $R_1$ and n have the same meanings as in the formula (I) and Hal represents a halogen atom, on an amine of formula:

  (III)

in which Het has the same meanings as in the formula (I).

This reaction is generally carried out in an inert solvent such as dimethylformamide, toluene or tetrahydrofuran, in the presence of a base such as an alkali metal bicarbonate or a trialkylamine, at the boiling temperature of the solvent.

The derivatives of formula (II), with the exception of those for which $R_1$ represents a residue of formula (C), may be obtained by the action of a derivative of formula:

  (IV)

in which $R_1$ has the same meanings as in the formula (I) on a dihalogenated derivative of formula:

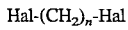  (V)

in which Hal represents a halogen atom, it being possible for the 2 halogen atoms to be identical or different, and n has the same meanings as in the formula (I).

This reaction is carried out in an inert solvent such as dimethylformamide, tetrahydrofuran or acetone, using sodium hydride or n-butyllithium, at a temperature between 20° C. and the boiling temperature of the solvent.

The derivatives of formula (II) for which $R_1$ represents a residue of formula (C) may be obtained by hydrolyzing a derivative of formula:

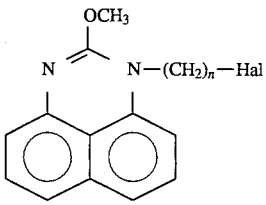  (VI)

in which Hal represents a halogen atom and n has the same meanings as in the formula (I).

This hydrolysis is carried out using an acid (for example hydrochloric acid) in an inert solvent such as an alcohol, water or a mixture of these solvents, at a temperature between 20° C. and the boiling temperature of the solvent.

The compounds of formula (VI) may be prepared by the action of a dihalogenated derivative of formula (V) on 2-methoxyperimidine.

This reaction is generally carried out in an inert solvent such as dimethylformamide, acetone or a mixture of such solvents, using sodium hydride, at a temperature between 20° C. and the boiling temperature of the solvent.

The compounds of formula (IV) are available commercially or my be obtained by applying or adapting the methods described by S. R. SALMAN, J. Chem. Eng. Data, 32, 39 (1987) in U.S. Pat. Nos. 4,132,725, DE 2,438,966 and in the examples.

The amines of formula (III) are available commercially or may be obtained by applying or adapting the methods described by D. K. YUNK et al., J. Med. Chem., 21, 1301 (1978); L. THUNUS et al., Ann. Pharm., 38, 353 (1980); L. GOOTES et al., Arzneim, Forsch., 17, 1145 (1963) and in Patent EP 350403.

The compounds of formula (I), with the exception of those for which $R_1$ represents a residue of formula (C), may also be prepared by the action of a derivative of formula (IV) on a halogenated derivative of formula:

  (VII)

in which Hal represents a halogen atom, n and Het have the same meanings as in the formula (I).

This reaction is generally carried out in the presence of a base such as an alkali metal hydride, an alkali metal hydroxide, an alkali metal bicarbonate or an alkali metal carbonate, optionally, in the presence of tetrabutylammonium bromide, in an inert solvent such as dimethylformamide or tetrahydrofuran, at a temperature between 20° C. and the boiling temperature of the solvent.

The halogenated derivatives of formula (VII) may be obtained by the action of an amine of formula (III) on a dihalogenated derivative of formula (V).

This reaction is generally carried out in an inert solvent such as dimethylformamide or acetonitrile, in the presence of a base such as an alkali metal carbonate, at a temperature between 20° C. and the boiling temperature of the solvent.

The reaction mixtures obtained by the various processes described above are treated using conventional physical (extraction, evaporation, distillation, chromatography and the like) or chemical (formation of salts and the like) methods.

The compounds of formula (I), in the form of a free base, may optionally be converted to addition salts with an inorganic or organic acid, by the action of such an acid in an organic solvent such as an alcohol, a ketone, an ether or a chlorine-containing solvent.

The compounds of formula (I) and their salts possess advantageous properties. These compounds possess serotonin-antagonising properties (5-HT$_2$ receptors) and are therefore useful in the treatment of disorders involving serotonin, in particular disorders of the central nervous system, the cardiovascular system and gastrointestinal disorders.

These compounds are in particular useful in the treatment of anxiety, sleep disorders, psychoses and in particular schizophrenia, migraine, asthma, hypertension and urticaria, as analgesics and as inhibitors of platelet aggregation.

The affinity of the compounds of formula (I) for the central receptor sites for serotonin (type S2) was determined using a technique based on that used by J. E. LEYSEN et al., Mol. Pharmacol., 21, 301 (1982) which consists in measuring the affinity of the products for the binding sites of tritiated ketanserin. In this test, the IC$_{50}$ of the compounds of formula (I) is generally less than 50 nM.

The compounds of formula (I) possess low toxicity. They are generally nontoxic at 300 mg/kg by the oral route when administered to mice in a single dose.

Compounds for which R$_1$ represents a residue of formula (D) and Her represents a radical 4-phenyl-1-piperazinyl whose phenyl ring is optionally substituted by a halogen atom and in particular fluorine or an alkyl or hydroxyl radical or a radical 4-phenyl-1,2,3,6-tetrahydro-1-pyridyl, are particularly useful.

The following compounds are of particular interest:

1,1-dimethyl-4-oxo-3-{3-(4-phenyl-1-piperazinyl) propyl}-1,2,3,4-tetrahydro-3,1-benzazasiline in the dihydrochloride form, 3-[3-{4-(4-methylphenyl)-1-piperazinyl}propyl]-1,1-dimethyl-4-oxo-1,2,3,4-tetrahydro-3,1-benzazasiline, 1,1-dimethyl-3-[3-{4-(4-hydroxyphenyl)-1-piperazinyl}propyl[-4-oxo-1,2,3,4-tetrahydro-3,1-benzazasiline, 1,1-dimethyl-3-[3-(4-phenyl-1,2,3,4-tetrahydro-1-pyridyl) propyl]-4-oxo-1,2,3,4-tetrahydro-3,1-benzazasiline, 1,1-dimethyl-5-fluoro-4-oxo-3-[3-(4-phenyl-1-piperazinyl) 3 -propyl]-1,2,3,4-tetrahydro-3,1 -benzazasiline, 4,4-dimethyl-2-[3-{4-(4-fluorophenyl)-1-piperazinyl}-propyl]1,2,3,4-tetrahydro-1-isoquinoline.

For therapeutic use, the compounds of formula (I) may be used as they are or in the form of pharmaceutically acceptable salts.

The following may be mentioned as pharmaceutically acceptable salts: the addition salts with inorganic acids such as hydrochlorides, sulphates, nitrates and phosphates, or with organic acids such as acetates, propionates, succinates, oxalates, benzoates, fumarates, maleares, methanesulphonates, isethionate, theophillineacetates, phenolphthalinates, salicylates and methylene-bis-β-oxynaphthoates, or the substituted derivatives of these derivatives.

The following examples, which are given with no limitation being implied, show how the invention may be implemented in practice.

EXAMPLE 1

1.35 g of 4-(4-fluorophenyl)piperazine, 1.84 g of 1-(3-chloropropyl)-2-perimidinone and 0.66 g of sodium bicarbonate, in 25 cm$^3$ of dry N,N-dimethylformamide are stirred at the reflux temperature of the solvent for 2 hours. The reaction mixture is cooled and poured into a mixture of 20 cm$^3$ of water and 25 cm$^3$ of dichloro-methane. The organic phase is decanted, washed with water (3×15 cm$^3$), dried over magnesium sulphate and concentrated to dryness under reduced pressure (2.7 kPa). The residue is chromatographed on a silica gel column under a pressure of 0.7 bar of nitrogen, eluting with ethyl acetate. 0.65 g of 1-{3-[4-(4-fluorophenyl)-1-piperazinyl]-propyl }-2-perimidinone is thus obtained; melting point =206° C.

1-(3-Chloropropyl)-2-perimidinone may be prepared in the following manner: 35 g of 3-(3-chloropropyl)-2-methoxyperimidine, 70 cm$^3$ of concentrated hydrochloric acid, 210 cm$^3$ of ethanol and 140 cm$^3$ water are heated at boiling temperature for 10 minutes. The reaction mixture is cooled to a temperature of about 20° C. and the precipitate is then filtered on sintered glass and dried. 32 g of 1-(3-Chloropropyl)-2-perimidinone are thus obtained; melting point =170° C.

3-(3-Chloropropyl)-2-methoxyperimidine may be prepared in the following manner: 49 g of 2-methoxyperimidine and 26.7 cm$^3$ of 1-bromo-3-chloropropane in 420 cm$^3$ of acetone and 42 cm$^3$ of N,N-dimethylformamide are heated at boiling temperature for 14 hours. The reaction mixture is cooled to a temperature of about 20° C. and then the precipitate is filtered on sintered glass and rinsed with 50 cm$^3$ diethyl oxide. The filtrate is concentrated to dryness under reduced pressure (2.7 kPa). The oil obtained is purified by chromatography on a silica gel column under a pressure of 0.7 bar of nitrogen, eluting with toluene. 34.9 g of 3-(3-chloropropyl)-2-methoxyperimidine are obtained (Rf 0.7-silica plate-toluene).

2-Methoxyperimidine may be prepared in the following manner: 50 g of 1,8-diaminonaphthalene and 42 g of methyl orthocarbonate are refluxed for 24 hours. The reaction mixture is cooled to a temperature of about 20° C. and then concentrated to dryness under reduced pressure (2.7 kPa). The residue is purified by chromatography on a silica gel column with dichloromethane as eluent. After washing with hexane, 39.5 g of 2-methoxyperimidine are obtained in the form of crystals which are used as they are in subsequent syntheses.

EXAMPLE 2

A mixture of 2.2 g of 3-anilino-1,2-benzisothiazole 1,1-dioxide, 2.1 g of 1-(3-chloropropyl)-4-(4-fluorophenyl)piperazine, 3.4 g of potassium carbonate, 1.1 g of tetrabutylammonium bromide and 25 cm$^3$ of dimethylformamide is refluxed for 24 hours. The mixture is then cooled to a temperature of about 20° C. The filtrate is evaporated to dryness at 40° C. under reduced pressure (10 mm of mercury; 1.35 kPa). The residue is taken up in 20 cm$^3$ of water and extracted with 75 cm$^3$ of dichloromethane. The organic phase thus obtained is dried over anhydrous magnesium-sulphate and evaporated to dryness at 40° C. under reduced pressure (20 mm of mercury; 2.7 kPa). The oil obtained is purified by flash chromatography on a silica column, under a nitrogen stream at moderate pressure (0.1–1.5 bar) with ethyl acetate as eluent. 1.0 g of a beige meringue is obtained which, when recrystallization from 10 cm$^3$ of hot ethanol yields 0.95 g of 3-{{3-[4-(4-fluorophenyl)-1-piperazinyl]propyl}phenylamino}-1,2-benzisothiazole 1,1-dioxide; melting point =134° C.

3-Anilino-1,2-benzisothiazole 1,1-dioxide may be prepared according to the method described by S. R. SALMAN, J. Chem. Eng. Data, 32, 391, 1987.

EXAMPLE 3

A mixture of 0.55 g of 3-amino-1,2-benzisothiazole 1,1-dioxide, 0.76 g of 1-(3-chloropropyl)-4-(4-fluorophenyl)-piperazine, 0.41 g of potassium carbonate and 10 cm$^3$ of dimethylformamide is heated for 11 hours at 60° C. The mixture is then cooled to a temperature of about 20° C. The filtrate is evaporated to dryness at 40° C. under reduced pressure (10 mm of mercury; 1.35 kPa). The residue is taken up in 10 cm$^3$ of water and extracted with three times 10 cm$^3$ of dichloromethane. The organic phase thus obtained is dried over anhydrous magnesium sulphate and evaporated to dryness at 40° C. under reduced pressure (20 mm of mercury; 2.7 kPa). The yellow solid obtained yields, when recrystallized from 10 cm$^3$ of hot acetonitrile, 0.85 g of 3-{{3-[4-(4-fluorophenyl)-l-piperazinyl]-propyl}amino}-1,2-benzisothiazole 1,1-dioxide; melting point =210° C.

3-Amino-1,2-benzisothiazole 1,1-dioxide may be prepared according to the method described by S. R. SALMAN, J. Chem. Eng. Data, 32, 391, 1987.

EXAMPLE 4

5.34 g of 3-(3-chloropropyl)-1,1-dimethyl-4-oxo-1,2,3,4-tetrahydro-3,1-benzazasiline, 6 cm$^3$ of triethylamine and 6.5 g of 1-phenylpiperazine in 100 cm$^3$ of toluene are heated at boiling temperature for 18 hours. The mixture is then adjusted to a temperature of about 20° C., taken up in 100 cm$^3$ of water and extracted with three times 50 cm$^3$ of dichloromethane. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol (90-10 by volume) mixture as eluent. 6 g of an orange oil (6 g) are obtained which, when dissolved in 30 cm$^3$ of diethyl ether and when chloroethane (4N) is added, yield 3.4 g 1,1-dimethyl-4-oxo-3- {3-(4-phenyl-1- piperazinyl)propyl}-1,2, 3,4-tetrahydro-3,1-benzazasiline in the dihydrochloride form; melting point =170° C.

3-(3-Chloropropyl)-1,1-dimethyl-4-oxo-1,2,3,4-tetrahydro-3,1-benzazasiline may be prepared in the following manner: 75 cm$^3$ of n-butyllithium (1.6 M in hexane are added to a solution of 19.1 g of 1,1-dimethyl-4-oxo-1,2,3,4-tetrahydro-3,1-benzazasiline in 300 cm$^3$ of tetrahydrofuran at –76° C., under a nitrogen stream. The reaction mixture is left for three hours at 0° C. 37.3 g of 1-chloro-3-bromopropane are then added and the mixture is stirred for 48 hours at a temperature of about 25° C. The reaction mixture is treated with 100 cm$^3$ of water and extracted with three times 50 cm$^3$ of dichloromethane. The combined organic phases are dried over magnesium sulphate and evaporated to dryness at 40° C. under reduced pressure (20 mm of mercury; 2.7 KPa). The residue obtained is purified by flash chromatography on a silica column under a nitrogen stream at moderate pressure (0.5–1.5 bar) with dichloromethane as eluent. 21 g of 3-(3-chloropropyl)-1,1-dimethyl-4-oxo-1,2,3,4-tetrahydro 3,1-benzazasiline are obtained in the form of an oil which is used as it is in subsequent syntheses.

1,1-Dimethyl-4-oxo-1,2,3,4-tetrahydro-3,1-benzazasiline may be obtained according to the process described in U.S. Pat. No. 4,132,725.

EXAMPLE 5

The procedure is carried out as in Example 4, using 2.7 g 3-(3-chloropropyl)-1,1-dimethyl-4-oxo-1,2,3,4-tetrahydro-3,1-benzazasiline, 4.3 g of 1-(4-fluorophenyl)-piperazine and 3.4 g triethylamine in 50 cm$^3$ of toluene. The mixture is heated at boiling temperature for 48 hours and then cooled to a temperature of about 25° C. The mixture is taken up in 100 cm$^3$ of water and extracted with 50 cm$^3$ of dichloromethane. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol (98-2 by volume) mixture as eluent. 4 g of an orange oil are obtained which, when dissolved in 50 cm$^3$ of chloroethane (4N) yield 3.6 g of a yellow solid. This solid is recrystallized from 120 cm$^3$ of a boiling acetonitrile-ethyl acetate mixture (50—50 by volume) and yields 1.4 g of 1,1-dimethyl-3-[3-{4-(4-fluorophenyl) 1-piperazinyl}-propyl]-4-oxo-1,2,3,4-tetrahydro-3,1-benzazasiline in the dihydrochloride form; melting point =209° C.

EXAMPLE 6

The procedure is carried out as in Example 4, using 2.9 g of 3-(3-chloropropyl)-1,1-dimethyl-4-oxo-1,2,3,4-tetrahydro-3,1-benzazasiline, 7.9 g of 4-(4-methylphenyl)-piperazine dihydrochloride and 9.3 cm$^3$ of triethylamine in 60 cm$^3$ of toluene. The mixture is heated at boiling temperature for 48 hours and then cooled to a temperature of about 25° C. The mixture is taken up in 100 cm$^3$ of water and extracted with three times 50 cm$^3$ of ethyl acetate. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol mixture (97.5-2.5 by volume) as eluent. 2.5 g of an orange oil are obtained which, when dissolved in 25 cm$^3$ of acetone and with the addition of 0.53 g of oxalic acid, yield 2.2 g of 3-[3- {4-(4-methylphenyl)-1-piperazinyl}propyl]-1,2-dimethyl-4-oxo-1,2,3,4-tetrahydro 3,1-benzazasiline in the oxalate form; melting point =153° C.

EXAMPLE 7

The procedure is carried out as in Example 4, using 2.9 g of 3-(3-chloropropyl)-1,1-dimethyl-4-oxo-1,2,3,4-tetrahydro-3,1-benzazasiline, 7.4 g of 1-(4-hydroxy-phenyl)-piperazine dihydrobromide and 6.1 cm³ triethylamine in 60 cm³ of toluene. The mixture is heated at boiling temperature for 48 hours and then cooled to a temperature of about 25° C. The mixture is taken up in 100 cm³ of water and extracted with three times 50 cm³ of ethyl acetate. The combined organic phases are dried over magnesium sulphate and evaporated to dryness at 40° C, under reduced pressure (20 mm of mercury; 2.7 KPa).

The residue is purified by flash chromatography on a silica column under a nitrogen stream at moderate pressure (0.5–1.5 bar) with a dichloromethane-methanol mixture (97.5–2.5 by volume) as eluent. After recrystallization from 50 cm³ of boiling acetonitrile, 1.8 g of 1,1-dimethyl-3-[3-{4-(4-hydroxyphenyl)-1-piperazinyl }-propyl]-4-oxo-1,2,3,4-tetrahydro-3,1-benzazasiline are obtained; melting point =170° C.

EXAMPLE 8

The procedure is carried out as in Example 4, using 2.9 g of 3-(3-chloropropyl)-1,1-dimethyl-4-oxo-1,2,3,4-tetrahydro-3,1-benzazasiline, 3.7 g of 4-phenylpiperidine and 3 cm³ of triethylamine in 60 cm³ of toluene. The mixture is heated at boiling temperature for 24 hours and then cooled to a temperature of about 25° C. The mixture is taken up in 100 cm³ of water and extracted with three times 50 cm³ of ethyl acetate. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with dichloromethane as eluent. 3.7 g of an orange oil are obtained which, when dissolved in 45 cm³ of acetone and with the addition of 0.4 g of oxalic acid, yield 2.9 g of 1,1-dimethyl-3-[3-(4-phenyl-1-piperidinyl)propyl ]-4-oxo-1,2,3,4-tetrahydro-3,1-benzazasiline in the oxalate form; melting point =153° C.

EXAMPLE 9

The procedure is carried out as in Example 4, using 2.9 g of 3-(3-chloropropyl)-1,1-dimethyl-4-oxo-1,2,3,4-tetrahydro-3,1-benzazasiline, 4.3 g of 4-phenyl-1,2,3,4,-tetrahydropyridine and 4.6 cm³ of triethylamine in 60 cm³ of toluene. The mixture is heated at boiling temperature for 24 hours and then cooled to a temperature of about 25° C. The mixture is taken up in 100 cm³ of water and extracted with three times 50 cm³ of ethyl acetate. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with dichloromethane as eluent. 1.7 g of an orange oil are obtained which, when dissolved in 16 cm³ of acetone and with the addition of 0.2 g of oxalic acid, yield 0.8 g of 1,1-dimethyl-3-[3-(4-phenyl-1,2,3,4-tetrahydro 1-pyridyl)propyl]-4-oxo-1,2,3,4-tetrahydro-3,1-benzazasiline in the oxalate form; melting point =182° C.

EXAMPLE 10

The procedure is carried out as in Example 4, using 2.9 g of 3-(3-chloropropyl)-1,1-dimethyl-4-oxo-1,2,3,4-tetrahydro-3,1-benzazasiline, 4.7 g of 4-(4-fluorophenyl)-1,2,3,4-tetrahydropyridine and 4.6 cm³ of triethylamine in 60 cm³ of toluene. The mixture is heated at boiling temperature for 24 hours and then cooled to a temperature of about 25° C. The mixture is taken up in 100 cm³ of water and extracted with three times 50 cm³ of ethyl acetate. The combined organic phases are dried over magnesium sulphate and evaporated to dryness at 40° C. under reduced pressure (20 mm of mercury; 2.7 KPa). The residue-is purified by flash chromatography on a silica column under a nitrogen stream at moderate pressure (0.5–1.5 bar) with a dichloromethane-methanol mixture (97.5–2.5 by volume) as eluent. 2.7 g of an orange oil are obtained which, when dissolved in 50 cm³ acetone and with the addition of 0.3 g of oxalic acid, yield 0.9 g of 1,1-dimethyl-3-[3-{4-(4-fluorophenyl) 1,2,3,4-tetrahydro-1-pyridyl}propyl]-4-oxo-1,2,3,4-tetrahydro-3,1-benzazasiline in the oxalate form; melting point =130° C.

EXAMPLE 11

0.65 g of 3-(3-chloropropyl)-1,1-dimethyl-7-fluoro-4-oxo-1,2,3,4-tetrahydro 3,1-benzazasiline, 0.7 cm³ of triethylamine and 0.74 g of 1-phenylpiperazine in 20 cm³ of toluene are heated at boiling temperature for 18 hours. The mixture is then adjusted to a temperature of about 20° C., taken up in 30 cm³ of water and extracted with two times 20 cm³ of ethyl acetate. The combined organic phases are dried over magnesium sulphate and evaporated to dryness at 40° C. under reduced pressure (20 nun of mercury; 2.7 KPa). The residue is purified by flash chromatography on a silica column under a nitrogen stream at moderate pressure (0.5–1.5 bar) with a dichloromethane-methanol mixture (98-2 by volume) as eluent. 0.5 g of an orange oil is obtained which, when dissolved in 10 cm³ of acetone and with the addition of 0.1 g of oxalic acid, yields 1,1-dimethyl-7-fluoro-4-oxo-3-[3-(4-phenyl-1-piperazinyl)propyl ]-1,2,3,4-tetrahydro-3,1-benzazasiline in the oxalate form; melting point =155° C.

3-(3-Chloropropyl)-1,1-dimethyl-7-fluoro-4-oxo-1,2,3,4-tetrahydro-3,1-benzazasiline may be prepared in the following manner: 9 cm³ of n-butyllithium (1.6 M in hexane) are added a solution of 2.5 g of 1,1-dimethyl-7-fluoro-4-oxo-1,2,3,4-tetrahydro-3,1-benzazasiline in 40 cm³ of tetrahydrofuran, at −76° C. under a nitrogen stream. The reaction mixture is left for three hours at 0° C. 4.53 g of 1-chloro-3-bromopropane are then added and the mixture is stirred for 48 hours at a temperature of about 25° C. The reaction mixture is treated with 100 cm³ of water and extracted with three times 25 cm³ of ethyl acetate. The combined organic phases are dried over magnesium sulphate and evaporated to dryness at 40° C. under reduced pressure (20 mm of mercury; 2.7 KPa). The residue obtained is purified by flash chromatography on a silica column under a nitrogen stream at moderate pressure (0.5–1.5 bar) with dichloromethane as eluent. 0.65 g of 3-(3-chloropropyl)-1,1-dimethyl-7-fluoro-4-oxo 1,2,3,4-tetrahydro-3,1-benzazasiline is obtained in the form of an oil which is used as it is in subsequent syntheses.

1,1-Dimethyl-7-fluoro-4-oxo-1,2,3,4-tetrahydro-3,1-benzazasiline may be prepared in the following manner: 260 cm³ n-butyllithium (1.6 M in hexane) are added to a solution of 27.1 g of N-tert-butyl-4-fluorobenzamide in 930 cm³ of tetrahydrofuran, at −76° C. under a nitrogen stream. The reaction mixture is left for three hours at 0° C. 39.75 g of dimethyl(chloromethyl)chlorosilane is then added and the mixture is stirred for 48 hours at 25° C. The mixture is treated with 1000 cm³ of water and extracted with three times 400 cm³ of ethyl acetate. The combined organic phases are dried over magnesium sulphate and evaporated to dryness at 40° C. under reduced pressure (20 mm of mercury; 2.7 KPa). The residue obtained is treated at 5° C. with 8 cm³ of sulphuric acid (d=1.87) and then stirred for two hours at 25° C. After neutralizing the medium with aqueous sodium hydroxide (d=1.33) and extracting with three times 50 cm³ of dichloromethane, the combined organic phases are dried over magnesium sulphate and evaporated to dryness at 40° C. under reduced pressure (20 mm of mercury; 2.7 KPa). The residue obtained is purifed by flash chromatography on a silica column under a nitrogen stream at moderate pressure (0.5–1.5 bar) with a dichloromethane-methanol mixture (97.5–2.5 by volume) as eluent. 5.05 g of 1,1-dimethyl-7-fluoro-4-oxo-1,2,3,4-tetrahydro 3,1-benzazasiline are obtained; melting point =95° C.

N- tert-Butyl-4 - fluorobenzamide may be prepared according to the method described by M. P. SPRATT and H. C. DORN, Ann. Chem., 56 (12), 2038 (1984).

EXAMPLE 12

The procedure is carried out as in Example 11, using 1.4 g of 3-(3-chloropropyl)-1,1-dimethyl-8-fluoro-4-oxo-1,2,3, 4-tetrahydro-3,1-benzazasiline 1.4 cm³ of triethylamine and 1.58 g of 1-phenylpiperazine in 45 cm³ of toluene. After purification-by flash chromatography on a silica column under a nitrogen stream at moderate pressure (0.5–1.5 bar) with a dichloromethane-methanol mixture (98.5–1.5 by volume) as eluent, 1.1 g of an oil is obtained which, when dissolved in 20 cm³ of acetone and with the addition of 0.24 g of oxalic acid, yields 1,1-dimethyl-8-fluoro-4-oxo-3-[3-(4-phenyl-1-piperazinyl) 3-propyl]-1,2,3,4-tetrahydro-3,1-benzazasiline in the oxalate form; melting point =187° C.

3-(3-Chloropropyl)-1,1-dimethyl-8-fluoro-4-oxo-1,2,3,4-tetrahydro-3,1-benzazasiline is obtained in a manner similar to that described in Example 4 for the preparation of 3-(3-chloropropyl)-1,1-dimethyl-4-oxo-1,2,3,4-tetrahydro-3,1-benzazasiline, but using 4.8 g of 1,1-dimethyl-8-fluoro-4-oxo-1,2,3,4-tetrahydro-3,1-benzazasiline, 17.2 cm³ of n-butyllithium, 8.7 g of 1-chloro-3-bromopropane and 70 cm³ of tetrahydrofuran. After purification by flash chromatography on a silica column under a nitrogen stream at moderate pressure (0.5–1.5 bar) with a dichloromethane-methanol mixture (98-2 by volume) as eluent, 2.75 g of 3-(3-chloropropyl)-1,1-dimethyl-8-fluoro-4-oxo- 1,2,3,4-tetrahydro-3,1-benzazasiline are obtained.

1,1-Dimethyl-8-fluoro-4-oxo-1,2,3,4-tetrahydro-3,1-benzazasiline may be obtained in a manner similar to that described in Example 11 for the preparation of 1,1-dimethyl-7-fluoro-4-oxo-1,2,3,4-tetrahydro-3,1-benzazasiline, but using 27.7 g of N-tert-butyl-3-fluorobenzamide, 266 cm³ of n-butyllithium, 40.6 g of dimethyllchloromethyl)chlorosilane and 950 cm³ of tetrahydrofuran. After purification, 7.7 g of an oil are obtained which, when treated with 8 cm³ of sulphuric acid (d=1.87) at 5° C., followed by neutralization with aqueous sodium hydroxide (d=1.33), yield after purification 4.8 g of 1,1-dimethyl-8-fluoro-4-oxo-1,2,3,4-tetrahydro-3,1-benzazasiline; melting point = 132° C.

N-tert-Butyl-3-fluorobenzamide is prepared according to the method described by M. P. SPRATT and H. C. DORN, Ann. Chem., 56 (12), 2038, (1984).

EXAMPLE 13

The procedure is carried out as in Example 11, using 1.15 g of 3-(3-chloropropyl)-1,1-dimethyl-5-fluoro-4-oxo-1,2,3, 4-tetrahydro-3,1-benzazasiline, 1.1 cm³ of triethylamine and 1.3 g of 1-phenylpiperazine in 23 cm³ of toluene (23 cc). After purification by flash chromatography on a silica column under a nitrogen stream at moderate pressure (0.5–1.5 bar) with a dichloromethane-methanol mixture (98.5–1.5 by volume) as eluent, 0.3 g of 1,1-dimethyl-5-(4-phenyl-1-piperazinyl)-3- [3-(4-phenyl-1-piperazinyl)-propyl]-4-oxo-1,2,3,4-tetrahydro-3,1-benzazasiline; melting point =166° C., and 0.3 g of an oil are obtained, which oil, when dissolved in 3 cm³ of acetone and treated with 0.24 g of oxalic acid, yield 1,1-dimethyl-5-fluoro-4-oxo-3-3-(4-phenyl-1-piperazinyl) 3-propyl]-1,2,3,4,-tetrahydro-3,1-benzazasiline in the oxalate form; melting point =99° C.

3-(3-Chloropropyl)-1,1-dimethyl-5-fluoro-4-oxo-1,2,3,4-tetrahydro-3,1-benzazasiline is obtained in a manner similar to that described in Example 11 for the preparation of 3-(3-chloropropyl)-1,1-dimethyl-7-fluoro-4-oxo-1,2,3,4-tetrahydro-3,1-benzazasiline, but using 3.15 g of 1,1-dimethyl-5-fluoro-4-oxo-1,2,3,4-tetrahydro-3,1-benzazasiline, 11.3 cm³ of n-butyllithium, 5.7 g of 1-chloro-3-bromopropane and 65 cm³ of tetrahydrofuran. After purification by flash chromatography on a silica column under a nitrogen stream at moderate pressure (0.5–1.5 bar) with a dichloromethane-methanol mixture (99.5–0.5 by volume) as eluent, 1.15 g of 3-(3-chloropropyl)-1,1-dimethyl-5-fluoro-4-oxo 1,2,3,4-tetrahydro-3,1-benzazasiline are obtained.

1,1,-Dimethyl-5-fluoro-4-oxo-1,2,3,4-tetrahydro-3,1-benzazasiline may be obtained in a manner similar to that described in Example 11 for the preparation of 1,1-dimethyl-7-fluoro-4-oxo-1,2,3,4-tetrahydro-3,1-benzazasiline but using 34.1 g of N-tert-butyl-1-fluorobenzamide, 328 cm³ of n-butyllithium, 50 g of dimethyl(chloromethyl)chlorosilane and 1170 cm³ of tetrahydrofuran. After purification, 4.4 g of an oil are obtained which, when treated with 10 cm³ of sulphuric acid (d=1.87) at 5° C., followed by neutralization with aqueous sodium hydroxide (d=1.33), yield after purification 3.15 g of 1,1-dimethyl-5-fluoro-4-oxo-1,2,3,4-tetrahydro 3,1-benzazasiline; melting point =133° C.

N-tert-Butyl-1-fluorobenzamide is prepared according to the method described by M. P. SPRATT and H. C. DORN, Ann, Chem., 56 (12), 2038, (1984).

EXAMPLE 14

1.25 g of 2-(3-chloropropyl)-4,4-dimethyl-1,2,3,4-tetrahydro-1-isoquinolinone, 1.4 cm³ of triethylamine and 1.62 g of 1-phenylpiperazine in 25 cm³ of toluene are heated at boiling temperature for 24 hours. The reaction mixture is then adjusted to a temperature of about 25° C., taken up in 50 cm³ of water and extracted with three times 25 cm³ of ethyl acetate. The organic phases are combined, dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol mixture (99-1 by volume) as eluent. 1.6 g of an orange oil are obtained which, when dissolved in 40 cm³ of acetone and with the addition of 0.43 g of oxalic acid, yield 1.4 g of 4,4-dimethyl-2-[3-(4-phenyl-1-piperazinyl)propyl ]-1,2,3,4-tetrahydro-1-isoquinolinone in the oxalate form; melting point =140° C.

2-(3-Chloropropyl)-4,4-dimethyl-1,2,3,4-tetrahydro-1-isoquinolinone may be obtained in the following manner: 25.7 cm³ of n-butyllithium (1.6 M in hexane) are added to a solution of 6 g of 4,4-dimethyl-1,2,3,4-tetrahydro-1-isoquinolinone in 120 cm³ of tetrahydrofuran, at −76° C. under a nitrogen stream. The reaction mixture is left for three hours at 0° C. 13 g of 1-chloro-3-bromopropane are then added and the mixture is stirred for 18 hours at a temperature of about 25° C. The reaction mixture is treated with 240 cm³ of water and extracted with three times 100 cm³ ethyl acetate. The combined organic phases are dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol mixture (99.5-0.5 by volume) as eluent. 3.9 g of 2-(3-chloropropyl)-4,4-dimethyl-1,2,3,4-tetrahydro 1isoquinolinone are obtained; melting point =131° C.

4,4-Dimethyl-1,2,3,4-tetrahydro-1-isoquinolinone may be obtained according to the process described in Patent DE 2,438,966.

EXAMPLE 15

The procedure is carried out as in Example 14 using 2.2 g of 2-(3-chloropropyl)-4,4-dimethyl-1,2,3,4-tetrahydro-1-isoquinolinone, 2.5 cm³ of triethylamine and 3.1 g of 1-(4-fluorophenyl)piperazine in 25 cm³ of toluene. The reaction mixture is heated at boiling temperature for 24 hours and then adjusted to a temperature of about 25° C., taken up in 50 cm³ of water and extracted with three times 25 cm³ of ethyl acetate. The organic phases are combined, dried over magnesium sulphate and evaporated to dryness at 40° C. under reduced pressure (20 mm of mercury; 2.7 KPa). The residue is purified by flash chromatography on a silica column under a nitrogen stream at moderate pressure (0.5–1.5 bar) with a dichloromethane-methanol mixture (99.5-0.5 by volume) as eluent. 3.2 g of an oil are obtained which, when dissolved in 20 cm³ of acetone and with the addition of 0.7 g of oxalic acid, yield 2.85 g of 4,4 -dimethyl-2-[3-{4-(4-fluorophenyl) 1-piperazinyl}propyl]-1,2,3,4-tetrahydro-1-isoquinolinone in the oxalate form; melting point =155° C.

EXAMPLE 16

The procedure is carried out as in Example 4 using 1.95 g of 4,4 -dimethyl-2-(3-chloropropyl)-3H-1,2,4-benzothiazasiline 1,1-dioxide, 2 g of 1-(4-fluorophenyl)piperazine, 1.5 cm³ of triethylamine and 35 cm³ of toluene. After purification by flash chromatography on a silica column under a nitrogen stream at moderate pressure (0.5–1.5 bar) with a dichloromethane-methanol mixture (98-2 by volume) as eluent, 2.4 g of an oil are obtained which, when dissolved in 40 cm³ of acetone and with the addition of 0.5 g of oxalic acid, yield 1.7 g of 4,4-dimethyl-2-{3-[4-(4-fluorophenyl)-1-piperazinyl ]propyl}-3H-1,2,4-benzothiazasiline 1,1-dioxide in the oxalate form; melting point =153° C.

4,4-Dimethyl-2-(3-chloropropyl)-3H-1,2,4-benzothiazasiline 1,1-dioxide may be obtained in a manner similar to that described in Example 4 for the preparation of 3-(3-chloropropyl)-1,1-dimethyl-4-oxo-1,2,3,4-tetrahydro-3,1-benzazasiline, but using 3.2 g of 4,4-dimethyl-3H-1,2,4-benzothiazasiline 1,1-dioxide, 10.5 cm³ of n-butyllithium, 5.3 g of 1-chloro-3-bromopropane and 50 cm³ of tetrahydrofuran. After purification by flash chromatography on a silica column under a nitrogen stream at moderate pressure (0.5–1.5 bar) with a dichloromethane-cyclohexane mixture (50—50 by volume) as eluent, 1.95 g of 4,4-dimethyl-2-(3-chloropropyl) 3H-1,2,4-benzothiazasiline 1,1-dioxide are obtained.

4,4-Dimethyl-3H-1,2,4-benzothiazasiline 1,1-dioxide may be prepared in the following manner: 4.6 g of N-tert-butyl-benzenesulphonamide in solution in 45 cm³ of tetrahydrofuran is treated at −76° C. with 37.5 cm³ of n-butyllithium. The reaction mixture is stirred for three hours at 0° C. and then 5.72 g of dimethyl-(chloromethyl)-chlorosilane is added. After stirring at 25° C. for 18 hours, the mixture is treated with 100 cm³ of water and extracted with three times 75 cm³ of ethyl acetate. The combined organic phases are dried over magnesium sulphate and evaporated to dryness at 40° C. under reduced pressure (20 mm of mercury; 2.7 KPa). The residue is treated with 3 cm³ of sulphuric acid (d=1.84) at 5° C. After neutralization with aqueous sodium hydroxide (d=1.33), extraction with three times 50 cm³ of dichloromethane and purification, 1.6 g of 4,4-dimethyl-3H-1,2,4-benzothiazasiline 1,1-dioxide are obtained; melting point =130° C.

N-tert-Butylbenzenesulphonamide may be prepared according to the process described in Patent EP 333557.

The medicinal products according to the invention consist of a compound of formula (I) in a free form or in the form of an addition salt with a pharmaceutically acceptable acid, in the pure state or in the form of a composition in which it is combined with any other pharmaceutically compatible product which may be inert or physiologically active. The medicinal products according to the invention may be administered orally, parenterally, rectally or topically.

Tablets, pills, powders (gelatin capsules, cachets) or granules may be used as solid compositions for oral administration. In these compositions, the active ingredient according to the invention may be mixed with one or more inert diluents such as starch, cellulose, sucrose, lactose or silica, under an argon stream. These compositions may also comprise substances other than diluents, for example one or more lubricants such as magnesium stearate or talc, a colorant, a coating (sugared pills) or a varnish.

Pharmaceutically acceptable solutions, suspensions, emulsions, syrups and elixirs containing inert diluents such as water, ethanol, glycerol, vegetable oils or paraffin oil_may be used as liquid compositions for oral administration. These compositions may comprise substances other than diluents, for example wetting, sweetening, thickening, flavoring or stabilizing products.

The sterile compositions for parenteral administration may be aqueous or nonaqueous solutions, suspensions or emulsions. Water, propylene glycol, polyethylene glycol, vegetable oils in particular olive oil, organic esters for injection, for example ethyl oleate or other suitable organic solvents, may be used, as a solvent or vehicle. These compositions may also contain adjuvants, in particular wetting, isotonizing, emulsifying, dispersing and stabilizing agents. Their sterilization may be performed in several ways, for example by aseptizing filtration, by incorporating sterilizing agents into the composition, by irradiation or by heating. They may also be prepared in the form of sterile solid compositions which may be dissolved at the time of use in sterile water or any other sterile medium for injection.

The compositions for rectal administration are suppositories or rectal capsules which contain, in addition to the active product, excipients such as cacao butter, semisynthetic glycerides or polyethylene glycols.

The compositions for topical administration may be for example creams, pommades, lotions, collyria, collutories, nasal drops or aerosols.

In human therapy, the compounds of the invention are particularly useful in the treatment of disorders involving serotonin and in particular disorders of the central nervous system, the cardiovascular system and intestinal disorders. They are in particular useful in the treatment of anxiety, sleep disorders, depression, psychoses and in particular schizophrenia, migraine, asthma, hypertension and urticaria, as analgesics and as inhibitors of platelet aggregation.

The doses depend on the desired effect and the administration route used; they are generally between 10 and 300 mg per day orally for an adult with unit doses ranging from 5 to 150 mg of active substance.

Generally, the physician will determine the appropriate dosage according to the age, weight and all the other factors specific to the individual to be treated.

The following examples illustrate the compositions according to the invention:

EXAMPLE A

Gelatin capsules containing a dose of 50 mg of the active product and having the following composition are prepared using conventional techniques:

| | |
|---|---|
| 1,1-Dimethyl-5-fluoro-4-oxo-3-[3-(4-phenyl-1-piperazinyl)-3-propyl]-1,2,3,4-tetrahydro-3,1-benzazasiline | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

EXAMPLE B

Tablets containing a dose of 50 mg of the active product and having the following composition are prepared using conventional techniques:

| | |
|---|---|
| 1,1-Dimethyl-4-oxo-3-{3-(4-phenyl-1-piperazinyl)propyl}-1,2,3,4-tetrahydro-3,1-benzazasiline | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxymethylcellulose, glycerine, titanium oxide (72-3.5-24.5) qs 1 finished coated tablet of | 245 mg |

EXAMPLE C

A solution for injection containing 10 mg of the active product and having the following composition is prepared:

| | |
|---|---|
| 1,1-Dimethyl-5-fluoro-4-oxo-3-{3-(4-phenyl-1-piperazinyl)propyl}-1,2,3,4-tetrahydro-3,1-benzazasiline | 10 mg |
| Benzoic acid | 80 mg |
| Benzyl alcohol | 0.06 cm³ |
| Sodium benzoate | 80 mg |
| Ethanol at 95% | 0.4 cm³ |
| Sodium hydroxide | 24 mg |
| Propylene glycol | 1.6 cm³ |
| Water | qs 4 cm³ |

Although the invention has been described in conjunction with specific embodiments, it is evident that many alternatives and variations will be apparent to those skilled in the art in light of the foregoing description. Accordingly, the invention is intended to embrace all of the alternative and variations that fall within the spirit and scope of the appended claims. The above references are hereby incorporated by reference.

We claim:

1. Compounds of formula:

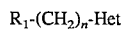

in which:

$R_1$ represents a residue of formula:

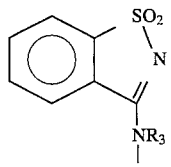

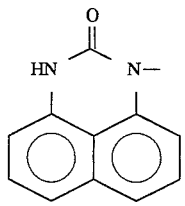

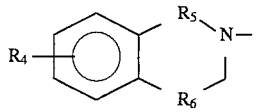

Het represents
- a radical 4-phenyl-1,2,3,6-tetrahydro-1-pyridyl whose phenyl ring is optionally substituted by a halogen atom or an alkyl, alkoxy or hydroxyl radical,
- a radical 4-phenylpiperidino whose phenyl ring is optionally substituted by a halogen atom or an alkyl, alkoxy or hydroxyl radical,
- a radical 4-phenyl-1-piperazinyl whose phenyl ring is optionally substituted by a halogen atom or an alkyl, alkoxy or hydroxyl radical, $R_3$ represents a hydrogen atom or a phenyl radical $R_4$ represents a hydrogen or a halogen atom or a Het residue, $R_5$ represents a carbonyl or sulphonyl radical, $R_6$ represents a radical Si $(CH_3)_2$ or C $(CH_3)_2$, n is equal to 1, 2, 3 or 4, with the exception of 3-{[2-(4-phenyl-1,2,3,6-tetrahydro-1-pyridyl) ethyl]amino}-1,2-benzisothiazole 1,1-dioxide, and it being understood that the alkyl and alkoxy radicals contain 1 to 4 carbon atoms in a linear or branched chain, and the salts of these compounds with an organic or inorganic acid.

2. Compounds of formula (I) according to claim 1 wherein $R_1$ represents a residue of formula (D) and Het represents a radical 4-phenyl-1-piperazinyl whose phenyl ring is optionally substituted by a halogen atom and in particular fluorine or an alkyl or hydroxyl radical or a radical 4-phenyl-1,2,3,6-tetrahydro-1-pyridyl.

3. A pharmaceutical composition for the treatment of ailments in which serotonin is implicated comprising an amount of at least one compound according to claim 1 effective to antagonize serotonin or a pharmaceutically acceptable salt thereof, in association with a compatible pharmaceutically acceptable carrier.

4. A method for the treatment of ailments in which serotonin is implicated which comprises administering to a subject in need of such treatment, an amount of a compound according to claim 1 effective to antagonize serotonin or a pharmaceutically acceptable salt thereof.

5. A pharmaceutical composition for the treatment of ailments in which serotonin is implicated comprising an effective amount of at least one of the following compounds to antagonize serotonin:

(a) 3-{3-[4-(4-fluorophenyl)-1-piperazinyl]propyl }phenylamino}-1,2-benziso-thiazole-1,1-dioxide;

(b) 1,2-dimethyl-4-oxo-3-{3-(4-phenyl-1-piperazinyl) propyl }-1,2,3,4-tetrahydro-3,1-benzazasiline in the dihydrochloride form;

(c) 3-[3-{4-(4-methylphenyl)-1-piperazinyl}propyl ]-1-1,1-dimethyl-4-oxo-1,2,3,4-tetrahydro-3,1-benzazasiline;

(d) 1,1-dimethyl-3-[3-{4-(4-hydroxyphenyl)-1-piperazinyl }propyl]-4-oxo-1,2,3,4-tetrahydro-3,1-benzazasiline;

(e) 1,1-dimethyl-3-[3-(4-phenyl-1,2,3,4-tetrahydro-1-pyridyl)propyl ]-4-oxo-1,2,3,4-tetrahydro-3,1-benzazasiline;

(f) 1,1-dimethyl-5-fluoro-4-oxo-3-[3-(4-phenyl-1-piperazinyl) 3-propyl]-1,2,3,4-tetrahydro-3,1-benzazasiline;

(g) 4,4-dimethyl-2-[3-{4-(4-fluorophenyl)-1-piperazinyl}-1,2,3,4-tetrahydro-1-isoquinoline;

or a pharmaceutically acceptable salt of at least one of said compounds; and a pharmaceutically acceptable carrier.

6. A compound according to claim 1, wherein said compound is 3-{3-[4-(4-fluorophenyl)-1-piperazinyl] propyl}phenylamino }-1,2-benziso-thiazole-1,1-dioxide or a pharmaceutically acceptable salt thereof.

7. A compound according no claim 1, wherein said compound is 1,1-dimethyl-4-oxo-3-{3-(4-phenyl-1-piperazinyl)propyl }-1,2,3,4-tetrahydro-3,1-benzazasiline or a pharmaceutically acceptable salt thereof.

8. The compound according to claim 7, wherein said compound is 1,1-dimethyl-4-oxo-3-{3-(4-phenyl-1-piperazinyl) propyl}-1,2,3,4-tetrahydro-3,1-benzazasiline in the dihydrochloride form.

9. A compound according to claim 1, wherein said compound is 3-[3-{4-(4-methylphenyl)- 1-piperazinyl}propyl]-1-1,1-dimethyl-4-oxo-1,2,3,4-tetrahydro-3,1-benzazasiline or a pharmaceutically acceptable salt thereof.

10. A compound according to claim 1, wherein said compound is 1,1-dimethyl-3-[3-{4-(4-hydroxyphenyl)-1-piperazinyl}propyl ]-4-oxo-1,2,3,4-tetrahydro-3,1-benzazasiline or a pharmaceutically acceptable salt thereof.

11. A compound according to claim 1, wherein said compound is 1,1-dimethyl-3-[3-(4-phenyl-1,2,3,4-tetrahydro-1-pyridyl) propyl]-4-oxo-1,2,3,4-tetrahydro-3,1-benzazasiline or a pharmaceutically acceptable salt thereof.

12. A compound according to claim 1, wherein said compound is 1,1-dimethyl-5-fluoro-4-oxo-3-[3-(4-phenyl-1-piperazinyl)-3-propyl ] -1,2,3,4-tetrahydro-3,1-benzazasiline or a pharmaceutically acceptable salt thereof.

13. A compound according to claim 1, wherein said compound is 4,4-dimethyl-2-[3-{4-(4-fluorophenyl)-1-piperazinyl}-propyl ]-1,2,3,4-tetrahydro-1-isoquinoline or a pharmaceutically acceptable salt thereof.

* * * * *

UNITED STATES PATENT AND TRADEMARK OFFICE
CERTIFICATE OF CORRECTION

PATENT NO. : 5,563,144
DATED : October 08, 1996
INVENTOR(S) : Dominique DAMOUR et al.

It is certified that error appears in the above-indentified patent and that said Letters Patent is hereby corrected as shown below:

Title page, Item [75], under "Inventors", line 3, "Jean-luc Malleron" should read --Jean-Luc Malleron--.

Claim 5, column 15, line 15, "1,2-dimethyl" should read --1,1-dimethyl--.

Claim 5, column 15, line 29, "azinyl) 3-propyl]" should read --azinyl)-3-propyl]--.

Claim 5, column 15, line 31, after "nyl}", insert -- -propyl]--.
Claim 7, column 16, line 5, "no" should read --to--

Signed and Sealed this

Twelfth Day of August, 1997

Attest:

BRUCE LEHMAN

*Attesting Officer*  *Commissioner of Patents and Trademarks*